United States Patent [19]
Lanquetin et al.

[11] Patent Number: 5,891,867
[45] Date of Patent: Apr. 6, 1999

[54] HORMONAL MEDICAMENTS AND THEIR USE FOR THE CORRECTION OF OESTROGENIC DEFICIENCIES

[75] Inventors: Michel Lanquetin, La Trinite; Jacques Paris, Nice; Jean-Louis Thomas, Charenton-le-pont, all of France

[73] Assignee: Laboratoire Theramex, Monaco

[21] Appl. No.: 817,329

[22] PCT Filed: Jul. 29, 1996

[86] PCT No.: PCT/IB96/00754

§ 371 Date: Apr. 24, 1997

§ 102(e) Date: Apr. 24, 1997

[87] PCT Pub. No.: WO97/04784

PCT Pub. Date: Feb. 13, 1997

[30] Foreign Application Priority Data

Aug. 1, 1995 [FR] France .................................. 95 09364

[51] Int. Cl.$^6$ ...................................................... A61K 31/56
[52] U.S. Cl. .............................................................. 514/170
[58] Field of Search ............................................... 514/170

[56] References Cited

FOREIGN PATENT DOCUMENTS 0136011  4/1985  European Pat. Off. .

OTHER PUBLICATIONS

Remington's Pharmaceutical Sciences (15th ed.) 1975 p. 914–915.

*Primary Examiner*—Phyllis G. Spivack
*Attorney, Agent, or Firm*—Bierman, Muserlian and Lucas

[57] ABSTRACT

A method of treating estrogen deficiencies in menopausal women by the oral administration of an estrogen alone followed by an estrogen progestogen combination and then a placebo.

12 Claims, No Drawings

HORMONAL MEDICAMENTS AND THEIR USE FOR THE CORRECTION OF OESTROGENIC DEFICIENCIES

The present invention relates to the field of chemotherapy.

More precisely, it relates to new pharmaceutical compositions formed from an estro-progestogenic combination for correction of estrogen deficiencies during natural or artificial menopauses.

It particularly relates to a trisequential estro-progestogenic combination, characterized in that it is made up of dosage units comprising only an oestrogen, dosage units comprising a combination of an estrogen and a progestogen and dosage units comprising only an excipient This combination is intended for administration by the oral route, and by using a particular formulation, it has been possible to be able to use estradiol, that is to say natural estrogen, by this route.

The progestogen used is a pure progestogen, such as nomegestrol acetate. As a result, it has been found that in such a combination, nomegestrol acetate does not cancel the natural effects of estradiol, while allowing an artificial cycle of very good quality to be obtained in the menopausal woman.

It specifically relates to a new estro-progestogenic medicament for correction of estrogen deficiencies, characterized in that it is formed from three different types of dosage units, which are intended for use in successive sequences, that is to say 17β-estradiol tablets, tablets comprising both 17β-estradiol and nomegestrol acetate, and placebo tablets comprising only excipient.

These administration units are intended for administration in accordance with the following sequences:
  the 17β-estradiol units for ten consecutive days
  the units of the combination of 17β-estradiol and nomegestrol acetate for fourteen consecutive days
  the placebo units for six days.

Consequently, the 17β-estradiol tablets will be administered from day D1 to day D10, the tablets of the combination of 17β-estradiol and nomegestrol acetate will be administered from day D11 to day D24, and the placebo tablets will be administered from day D25 to day D30.

According to a particular embodiment, the dosage units of oestradiol comprise an amount of active principle ranging from 1 to 3 mg, the dosage units containing the combination of 17β-estradiol and nomegestrol acetate comprise an amount of 17β-estradiol ranging from 1 to 3 mg and an amount of nomegestrol acetate ranging from 1.5 to 6 mg. Preferably, the dosage units of estradiol comprise 1 to 2 mg of 17β-estradiol and the dosage units of the estro-progestogenic combination comprise 1 to 2 mg of 17β-estradiol and 2.5 to 5 mg of nomegestrol acetate. Specifically, the optimum formulations comprise 1.5 mg of 17β-estradiol or a combination of 1.5 mg of 17β-estradiol and 3.75 mg of nomegestrol acetate.

This sequential mode of administration is intended to compensate functional disorders caused by hypoestrogenia associated with menopause or with premenopause. In particular, it is aimed at re-establishing an endometrial cycle in menopausal women, in particular those treated with 1 or 2 mg of 17β-estradiol.

First clinical trial:

35 menopausal patients were studied in order to specify the best dose of nomegestrol acetate (N) to be associated with estradiol to obtain menstrual cycles of quality with good luteal impregnation of the endometrium.

These patients were monitored in 6 different centres and received: initially, in an open trial, 17β-estradiol by itself (in an amount of 1 or 2 mg/day, the gynecologist having to adjust the dosages as a function of the clinical response) for 2 months; subsequently, under blind conditions, one of the following combinations for 4 months (estradiol for 10 days, combination for the following 14 days, pause of 7 days).

| | | | |
|---|---|---|---|
| ● | group A: O2 2mg - | N5 mg | (n = 6) |
| ● | group B: O2 2mg - | N2.5 mg | (n = 8) |
| ● | group C: O2 2mg - | N5 mg | (n = 9) |
| ● | group D: O2 2mg - | N2.5 mg | (n = 7) |
| ● | group E: O2 2mg - | N1.25 mg | (n = 5) |

(O2: 17β-estradiol N: nomegestrol acetate)

In 6 cases, the estradiol dosage was adjusted and differed between the two treatment phases.

Two histological approaches were realized, the traditional one comprised semi-quantitative differentiation of the parameters of estrogenization and of endometrial luteinization; the other comprised evaluation of the same parameters quantitatively with the aid of a computerized image analyzer system.

At the time of the study, the women of the various groups did not differ in any important parameter (age, height, weight, arterial pressure and length of time of the menopause).

The results obtained after 4 months of sequential treatment with 17β-estradiol/nomegestrol acetate showed no statistically significant difference in a general manner between the groups:
  most often, no reappearance of hot flushes
  appearance of mastodynia more frequent in the two groups of 2 mg of estradiol than in the three groups of 1 mg (4 cases out of 13 and 2 cases out of 18 respectively, these last two in group E).
  no pain on palpation of the breasts, no nodule was found during the six months of monitoring.
  occurrence of deprivation bleeding at the end of all the treatment cycles, except in 1 case of group A and in 2 cases of group C, groups having 5 mg of nomegestrol acetate in their composition. The delay in the occurrence of bleeding after the treatment was stopped, its duration and its heaviness were recorded.

At the histological level, there was no significant difference between the two estroprogestogen combinations, but they both differ from placebo by the existence of a higher number of endometria of secretory appearance, whereas there is a majority of proliferative endometria under placebo.

As regards the occurrence of clinical symptoms of hyperestrogenia (mastodynia, pain and tension on palpation of the breasts, pelvic abdominal distension), there was no significant difference between the three groups.

The general tolerance is equivalent in the three groups. There is no variation in weight nor in systolic and diastolic arterial pressure after three months of treatment. In the placebo group, 5 patients show one or more undesirable effects, 6 in the group of 1 mg of O2/2.5 mg of NOM and 3 in the group of 1.5 mg of O2/3.75 mg of NOM.

As regards the lipid parameters, the two progestogen combinations caused a significant drop in total cholesterol, LDL cholesterol and Lpa. In the group of 1.5 mg of O2/3.75 mg of NOM, a significant increase in apolipoprotein Al and an increase close to statistical significance in HDL cholesterol is found. There is no difference between the two combinations. The glycemia and insulinemia do not vary significantly.

As regards the coagulation factors, no significant change in antithrombin III, fibrinogen, fragment 1+2, prothrombin and total and free protein S was found. Protein C dominated slightly in the group of 1 mg of O2/2.5 mg of NOM, but did not vary significantly in the group of 1.5 mg of O2/3.75 mg of NOM. The plasminogen was increased significantly in the patients treated with the two estroprogestogen combinations.

Thus, although no statistically significant difference could be detected between the various combinations, whatever the parameter studied, either clinical or histological, the results obtained suggest that group D gives the best results.

Second clinical trial:

In another trial, randomized over 57 patients divided into three groups, the following were administered in parallel to three groups of 19 patients in an amount of one tablet per day:

tablets of 1 mg of 17β-estradiol for 24 days combined with 2.5 mg of nomegestrol acetate for the last 14 days tablets of 1.5 mg of 17β-estradiol for 24 days combined with 3.75 mg of nomegestrol acetate for the last 14 days a placebo On inclusion, no significant difference between the 3 groups was recorded as regards age, length of time of the menopause, length of time of hot flushes and plasma concentrations of FSH and estradiol.

The 3 treatments are effective on hot flushes, but the two active treatments differ from placebo as regards their effect on the intensity both at the 1st month and at the 3rd month. On the other hand, no significant difference between the two combinations was detected. As regards the frequency of hot flushes occurring during the night, there is a statistically significant difference between the group of 1.5 mg of O2/3.75 mg of NOM and the other two at the first month.

The global score of the climacteric symptomatology decreases significantly, whether at 1 or at 3 months. There is a statistically significant difference between each of the two estroprogestogen combinations and placebo at 1 month and at 3 months.

At the level of the quality of the cycles, there is no difference regarding the frequency of the occurrence of deprivation bleeding, spotting or menorrhagia between the two treated groups. The same applies to the delay in the appearance of periods, their duration and their heaviness.

At the histological level, the two treated groups are identical but different from placebo ($p<0.001$) with a majority of secretory endometria in the treated groups and a majority of proliferative endometria in the placebo group. No hyperplasia from endometria was found.

As regards the occurrence of mastodynias, abdominopelvic distension, pain and tension on palpation of the breasts, there is no significant difference between the three groups.

The general tolerance is equivalent in the three groups. There is no variation in weight nor in systolic and diastolic arterial pressure after three months of treatment. In the placebo group, 5 patients show one or more undesirable effects; 6 in the group of 1 mg of O2/2.5 mg of NOM and 3 in the group of 1.5 mg of O2/3.75 mg of NOM.

Regarding the lipid parameters (total cholesterol, C-HDL, C-LDL, apolipoproteins A1 and B, Lpa, triglycerides), only Lpa significantly drops in the group of 1 mg of 02/2,5 mg of NOM. In the group of 1,5 mg of 02/3,75 mg of NOM, the decrease of Lpa is close to significatively ($p=0,055$), a significative increase in apolipoprotein A1 ($p=0,005$) and increase of the C-HDL close to significativity, a significative decrease of total cholesterol ($p<0,05$) of C-LDL ($p<0,01$) and the ratio of atherogenic character CT/C-HDL and ApoB/ApoA$_1$ (respectively $p<0,001$ and $p<0,01$) are found. There is no difference between the two treated groups. The two treated groups only differ from placebo by the increase of apolipoproteins A$_1$. The glycemia and insulinemia do not significantly vary.

As regards the coagulation factors, antithrombin III and fibrinogen, no difference between each treated group and placebo group was found.

The plasma concentrations of estradiol are lower with 1 mg of O2 (35.5±6.67 pg/ml) than with 1.5 mg of O2 (72.5±6.74 pg/ml). There is a significant difference ($p<0.05$) in the group of 1.5 mg of O2/3.75 mg of NOM with respect to the placebo group and with respect to the group of 1 mg of O2/2.5 mg of NOM; as regards the sex hormone-binding protein: the increase is greater in the group of higher dosage.

IN CONCLUSION:

The two formulations are effective from the first month on climacteric symptomatology, and their efficacy differs from that of placebo. However, as regards the frequency of hot flushes during the night, there is a significant difference between the "high dose" group and the other two groups at the 1st month.

No difference between the three groups was recorded as regards gynaecological tolerance (mastodynia, quality of cycles and of periods) and general tolerance (weight and arterial pressure).

Third series of studies:

In a third series of clinical trials, a comparative study of the therapeutic efficacy of two estroprogestogen combinations comprising different doses of 17β-estradiol and nomegestrol acetate in comparison with placebo in the treatment of hot flushes in menopausal women was carried out.

This is a multicentre double-blind trial, randomized in three parallel groups:

83 patients were included in the study, 24 of whom were randomized in the placebo group, 29 in the group of 1 mg of O2/2.5 mg of NOM and 30 in the group of 1.5 mg of O2/3.75 mg of NOM, the study relating to menopausal women having an amenorrhoea of more than 3 months accompanied by hot flushes.

The products tested were:

tablets of 1 mg of 17β-estradiol for 24 days with 2.5 mg of nomegestrol acetate in the last 14 tablets tablets of 1.5 mg of 17β-estradiol for 24 days with 3.75 mg of nomegestrol acetate in the last 14 tablets in comparison with a placebo tablet administered for the same length of time.

On inclusion, analysis showed no difference between the three groups as regards the age of the patients, the length of time of the menopause and the level of FSH and estradiol.

The results of this trial confirm the clinical data observed during the preceding trials, demonstrating the efficacy of the two estroprogestogen combinations on climacteric symptomatology and on diurnal and, in particular, nocturnal hot flushes. There is no difference between them, but they prove to be superior to placebo in the majority of the clinical criteria studied. In the two groups under hormone treatment, no difference regarding the frequency of the occurrence of deprivation bleeding, its flow (d), its duration and its heaviness, nor for the frequencies of the occurrence of intercurrent bleeding (menorrhagia and spotting) is found. The tolerance was equivalent in the three groups studied.

Fourth clinical trial:

Comparative study of the therapeutic efficacy of a placebo and of two estroprogestogenic combinations comprising different doses of 17β-estradiol and nomegestrol acetate on the biological markers of bone restructuring in menopausal women.

The methodology is that of a multicentre double-blind trial randomized over 3 parallel groups.

The number of subjects is 117 (38 in the placebo group, 39 in the group of 1 mg of O2/2.5 mg of NOM and 40 in the group of 1.5 mg of O2/3.75 mg of NOM). The subjects are menopausal women with an amenorrhea of longer than 6 months.

PRODUCT, DOSE AND MODE OF ADMINISTRATION:

tablets of 1 mg of 17β-estradiol for 24 days with 2.5 mg of nomegestrol acetate in the last 14 tablets tablets of 1.5 mg of 17β-estradiol for 24 days with 3.75 mg of nomegestrol acetate in the last 14 tablets placebo tablets Results:

The clinical data collected in this trial confirm the results of the preceding trials, demonstrating that the two combinations reduce the frequency of hot flushes and enable an artificial cycle to be re-established.

No significant difference was found between the three groups as regards the clinical and biological tolerance.

The two estroprogestogenic combinations tested differ from placebo in their ability to lower significantly the blood alkaline phosphatases and the pyridinoline/creatinine and deoxypyridinoline/creatinine ratios in the urine, whereas these parameters increase in the placebo group.

These results obtained in the short-term thus indicate that the hormone combinations tested are able to check the increased bone restructuring after the menopause. A beneficial effect in the prevention of postmenopausal osteoporosis can be predicted from this.

Intragroup analysis of the plasma markers of bone restructuring show a significant reduction in osteocalcin ($p<0.02$) and a reduction close to significance in alkaline phosphatases in the group of 1 mg of O2/2.5 mg of NOM.

Comparison of the placebo group and the two treated groups reveals a significant difference ($p<0.05$) as regards alkaline phosphatases and a difference close to significance ($p=0.065$) as regards their osseous isoenzymes. There is no difference between the two treated groups.

Regarding the urinary markers, there is no difference between the three groups at the level of the calcium/creatinine and hydroxyproline/creatinine ratios. At the level of the pyridinoline/creatinine ratio, there is a significant difference between the group of 1 mg of O2/2.5 mg of NOM and the placebo group when the percentage variation with respect to the inclusion value is compared.

The global score of the climacteric symptomatology decreases significantly in the three groups, with no difference between them.

There is no difference between the two treated groups as regards the frequency of the occurrence of deprivation bleeding, spotting and metrorrhagia. However, two patients stopped the treatment because of metrorrhagia in the group of 1.5 mg of O2/3.75 mg of NOM, while none did in the other two groups. As regards the duration of periods, there is no difference between the two treated groups, whereas the delay in appearance is shorter in the group of 1 mg of O2/2.5 mg of NOM than in the high dose group ($p<0.05$).

As regards mastodynia, abdomino-pelvic distension, pain and tension on palpation of the breasts, although their occurrence had a tendency to be more frequent in the group of 1.5 mg of O2/3.75 mg of NOM, the difference from the other two groups is not significant.

The tolerance is equivalent in the three groups, as is the incidence of discontinuations of treatment. One or more secondary effects were encountered in 5 patients of the placebo group, 13 of the group of 1 mg of O2/2.5 mg of NOM and 12 of the group of 1.5 mg of O2/3.75 mg of NOM.

The systolic and diastolic arterial pressures are not changed, whatever the treatment. There is a significant increase in weight ($p<0.01$) in the group of 1.5 mg of O2/3.75 mg of NOM in the course of the trial; however, there is no significant difference between the three groups either in the weight level or in the arterial pressure.

As regards the biological parameters, there is an increase close to significance in the glycemia in the group of 1 mg of O2/2.5 mg of NOM and a reduction close to significance in cholesterol in the placebo group. Comparison of the metabolic biological parameters did not demonstrate a significant difference between the three groups.

The plasma concentrations of estradiol are lower with 1 mg of O2 (49.6±8.09 pg/ml) than with 1.5 mg of O2 (60.8±10.24 pg/ml).

IN CONCLUSION:

As regards the majority of the markers of bone restructuring, there is no difference between the two treated groups and the placebo group, with the exception of the percentage variation in the pyridinoline/creatinine ratio with respect to that at inclusion; there is a difference between the placebo group and the "low dose" group.

Example of a pharmaceutical composition according to the invention:

A/. Estradiol tablets:

| | |
|---|---|
| Estradiol | 1.500 g |
| Polyvinylpyrrolidone (Kollidon 25 from BASF) | 13.500 g |
| Lactose | 135.795 g |
| Microcrystalline cellulose (Avicel PH 101) | 26.250 g |
| Glyceryl palmitostearate (Precirol) | 2.775 g |
| Anhydrous colloidal silica (Aerosil 200) | 1.000 g |
| Crospovidone (Polyplasdone XL) | 4.000 g |
| Coloring agent for 1,000 finished tablets of 0.185 g | 0.180 g |

Production is carried out in two stages:

a) preparation of a premix

| | |
|---|---|
| Estradiol hemihydrate (with an average hydration of 3.2%) | 0.4644 4.050 kg |
| Polyvinylpyrrolidone | 3.532 kg |
| Isopropyl alcohol | 2.025 kg |
| Purified water | 18.000 kg |
| Lactose | 2.250 kg |
| Microcrystalline cellulose. | |
| Total after granulation and drying | #24.764 kg | b) Preparation of the final mixture:

| | |
|---|---|
| | #24.7640 kg |
| Granulated and dried premix | 0.8325 kg |
| Glyceryl palmitostearate | 0.300 kg |
| Anhydrous colloidal silica | 1.200 kg |
| Crosslinked polyvinylpyrrolidone | 5.6250 kg |
| Microcrystalline cellulose | 22.7385 kg |
| Lactose | 0.0540 kg |
| Coloring agent | |
| | 55.5000 kg |

Example of a pharmaceutical composition according to the invention:

B/. Tablets of estradiol and nomestrol acetate (1.5 mg of oestradiol and 3.75 mg of nomegestrol acetate per tablet):

| | |
|---|---|
| Nomegestrol acetate | 0.3750 kg |
| Premix according to Aa) | 8.9285 kg |
| Lactose | 6.400 kg |
| Avicel PH 101 | 1.8010 kg |
| Precirol ATO 5 | 0.2775 kg |
| Polyplasdone XL | 0.6000 kg |
| Coloring agent | 0.0180 kg |
| Aerosil 200 | 0.1000 kg |
| for 100,000 finished tablets of average weight 0.185 g. | |

We claim:

1. A method of treating estrogen deficiencies and reestablishing an endometrial cycle in menopausal women comprising administering orally to menopausal women in three different sequences an estrogen alone followed by an estrogen progestogen combination and then a placebo over the duration of a month.

2. The method of claim 1 wherein the estrogen is 17β-estradiol.

3. The method of claim 2 wherein the 17β-estradiol, an ester thereof or a conjugation product of equine estrogen is administered at 1 to 3 mg per unit dose.

4. The method of claim 3 wherein the 17β-estradiol, an ester thereof or a conjugation product of equine estrogens, is administered at 1 to 2 mg per unit dose.

5. The method of claim 1 wherein the progestogen is nomegestrol acetate.

6. The method of claim 1 wherein the combination of estrogen and a progestogen is administered in the form of tablets of 17β-estradiol, an ester thereof or a conjugation product of equine estrogens, with nomagestrol acetate.

7. The method of claim 6 wherein the 17β-estradiol, an ester thereof or a conjugation product of equine estrogens, is administered at 1 to 3 mg per unit dose and the nomegestrol acetate is administered at 1.5 to 6 mg per unit dose.

8. The method of claim 7 wherein the 17β-estradiol, an ester thereof or a conjugation product of equine estrogens, is administered at 1 to 2 mg per unit dose and the nomegestrol acetate is administered at 2.5 to 5 mg per unit dose.

9. The method of claim 1 wherein the placebo is administered in the form of tablets for six days consecutively.

10. The method of claim 1 wherein the estrogen alone is administered in the form of tablets of 17β-estradiol, an ester thereof or a conjugation product of equine estrogens for a period of 10 days.

11. A process for the preparation of tablets of 17β-estradiol, an ester thereof or a conjugation product of equine estrogens of claim 10, consisting of preparing first a premix made of estradiol hemihydrate or an ester thereof or a conjugation product of equine estrogens hemihydrate, polyvinylpyrrolidone, isopropyl alcohol, purified water, lactose and microcrystalline cellulose, granulating the premix and drying, and preparing the final mixture made of granulated and dried premix, of glycerol palmitostearate, anhydrous colloidal silica, crosslinked polyvinylpyrrolidone, microcrystalline cellulose, lactose and coloring matter.

12. A process for the preparation of tablets of 17β-estradiol, an ester thereof or a conjugation product of equine estrogens, which consists of adding the premix as defined in claim 11 with nomegestrol acetate, pharmaceutical diluents, coloring matter and colloidal silica to obtain tablets of 17β-estradiol, or an ester thereof or a conjugation product of equine estrogens, with nomegestrol acetate.

* * * * *